(12) United States Patent
Sun et al.

(10) Patent No.: US 12,280,175 B2
(45) Date of Patent: Apr. 22, 2025

(54) FORMULATIONS AND PROCESSES TO GENERATE REPELLENT SURFACES ON MEDICAL DEVICES

(71) Applicant: SPOTLESS MATERIALS INC., State College, PA (US)

(72) Inventors: Nan Sun, State College, PA (US); Birgitt Boschitsch, State College, PA (US)

(73) Assignee: SPOTLESS MATERIALS INC., State College, PA (US)

( * ) Notice: Subject to any disclaimer, the term of this patent is extended or adjusted under 35 U.S.C. 154(b) by 0 days.

(21) Appl. No.: 18/543,266

(22) Filed: Dec. 18, 2023

(65) Prior Publication Data

US 2024/0181131 A1    Jun. 6, 2024

Related U.S. Application Data

(62) Division of application No. 17/020,409, filed on Sep. 14, 2020, now Pat. No. 11,883,558.

(Continued)

(51) Int. Cl.
*A61L 24/06* (2006.01)
*A61L 27/34* (2006.01)

(52) U.S. Cl.
CPC ........... *A61L 27/34* (2013.01); *A61L 2420/02* (2013.01); *A61L 2420/06* (2013.01)

(58) Field of Classification Search
CPC .............................. A61L 2420/02; A61L 27/34
See application file for complete search history.

(56) References Cited

U.S. PATENT DOCUMENTS

| | | | | |
|---|---|---|---|---|
| 4,319,571 A | * | 3/1982 | Winchell | A61F 5/445 604/342 |
| 4,844,986 A | * | 7/1989 | Karakelle | A61L 29/085 427/407.1 |

(Continued)

FOREIGN PATENT DOCUMENTS

| | | |
|---|---|---|
| CN | 107207981 A | 9/2017 |
| CN | 110072694 A | 7/2019 |

(Continued)

OTHER PUBLICATIONS

U.S. Appl. No. 17/020,409, filed Sep. 14, 2020.

(Continued)

*Primary Examiner* — Cachet I Proctor
(74) *Attorney, Agent, or Firm* — BakerHostetler

(57) ABSTRACT

All-in-one formulations for preparing repellent coatings on surfaces of substrates include (i) one or more reactive components that can form a bonded layer on a surface in which the bonded layer comprises an array of compound each compound having one end bound to a surface and an opposite end extending away from the surface; (ii) an optional catalyst; (iii) a solvent; and (iv) a lubricant. A repellent coating can be formed from such formulations on substrate surfaces by drying the formulation on the surface to substantially remove the solvent and to form a bonded layer on the surface with the lubricant stably adhered to the bonded layer. The formulations can be applied to surfaces of ceramics, glasses, metals, alloys, composites, polymers or combinations thereof such as ceramic or metal plumbing fixtures, surfaces of glass substrates including mirrors, windshields, windows, surfaces composed of one or more polymers, medical devices such as ostomy appliances, etc.

16 Claims, 4 Drawing Sheets

Related U.S. Application Data

(60) Provisional application No. 62/992,589, filed on Mar. 20, 2020, provisional application No. 62/935,887, filed on Nov. 15, 2019, provisional application No. 62/900,207, filed on Sep. 13, 2019.

(56) References Cited

U.S. PATENT DOCUMENTS

| | | | |
|---|---|---|---|
| 5,330,794 | A | 7/1994 | Bosco et al. |
| 5,366,768 | A * | 11/1994 | Kasari .................. B05D 5/068 427/407.1 |
| 6,432,181 | B1 | 8/2002 | Ludwig |
| 6,676,733 | B2 | 1/2004 | Ludwig et al. |
| 6,994,890 | B2 | 2/2006 | Ohlhausen et al. |
| 7,651,485 | B2 * | 1/2010 | Fattman ................. C09J 183/04 604/339 |
| 7,754,004 | B2 | 7/2010 | Ohlhausen et al. |
| 9,121,306 | B2 | 9/2015 | Aizenberg et al. |
| 10,240,067 | B2 | 3/2019 | Kim et al. |
| 10,968,353 | B2 | 4/2021 | Wong et al. |
| 2002/0128419 | A1* | 9/2002 | Terry ..................... A61L 31/10 528/28 |
| 2004/0260048 | A1* | 12/2004 | Itagaki ................. C09D 183/04 528/33 |
| 2014/0342954 | A1 | 11/2014 | Ingber et al. |
| 2015/0173883 | A1* | 6/2015 | Ingber ................... A61L 31/028 604/9 |
| 2015/0175814 | A1 | 6/2015 | Aizenberg et al. |
| 2015/0210951 | A1* | 7/2015 | Aizenberg ............. B05D 5/08 141/1 |
| 2016/0177129 | A1 | 6/2016 | McCarthy et al. |
| 2018/0148599 | A1* | 5/2018 | Bandyopadhyay .. C09D 5/1693 |
| 2018/0187022 | A1 | 7/2018 | Aizenberg et al. |
| 2018/0237659 | A1* | 8/2018 | Kim ....................... C08G 77/28 |
| 2018/0327608 | A1 | 11/2018 | Aizenberg et al. |
| 2018/0327684 | A1 | 11/2018 | Kim et al. |
| 2019/0016903 | A1* | 1/2019 | Wong ..................... E03D 1/01 |
| 2019/0100681 | A1 | 4/2019 | Kim et al. |

FOREIGN PATENT DOCUMENTS

| | | |
|---|---|---|
| KR | 10-0887573 B1 | 3/2009 |
| KR | 10-1544313 B1 | 8/2015 |
| WO | 2005/014742 A1 | 2/2005 |
| WO | 2012/100100 A2 | 7/2012 |
| WO | 2018/094161 A1 | 5/2018 |
| WO | 2013/106588 A1 | 7/2019 |
| WO | 2019/222007 A1 | 11/2019 |
| WO | 2019/237093 A1 | 12/2019 |

OTHER PUBLICATIONS

First Chinese Office Action issued in Chinese Patent Application No. 202080064547.1 mailed Oct. 21, 2022, with English Translation.

CN Office Action 202080064547.1 dated Oct. 21, 2022, 9 pages.

Wang, et al., "Covalently Attached Liquids: Instant Omniphobic Surfaces with Unprecedented Repellency," Angew. Chem. Int. Ed. 2016, 55, pp. 244-248.

Maccallum et al., "Liquid-Infused silicone as a biofouling-free medical material", ACS biomaterials Science and Engineering, 2015, 1; pp. 43-51 (Year: 2015).

Cui et al., "Dynamic polymer systems with self-regulated secretion for control of surface properties and material healing", Nat Mater. Aug. 2015; 14(8); pp. 790-795. doi: 10.1038/nmat4325. Epub Jun. 22, 2015. (Year: 2015).

International Search Report issued in corresponding International Application No. PCT/US2020/050618 dated Jan. 1, 2021.

International Search Report issued in corresponding International Application No. PCT/US2020/050618 dated Dec. 29, 2020.

Wooh et al., "Silicon Brushes: Omniphobic Surfaces with Low Sliding Angles", Angewandle Chemie, 2016, vol. 55, pp. 6822-6824.

Esra et al., "Transparent, fluorine-free, heat-resistant, water repellent coating by infusing slippery silicone oil on polysiloxane nanofilamenl layers prepared by gas phase reaction of n-propyltrichlorosilane and methyltrichlorosilane," Colloids and Surfaces A, 2019 [Available online Sep. 25, 2018], vol. 560, pp. 223-232.

Yao et al., "Fluorogel Elastomers with Tunable Transparency, Elasticity, Shape-Memory, and Antifouling Properties", Angewandte Chemie Int. Ed. 53, pp. 4418-4422, (2014).

Amini et al., "Preventing mussel adhesion using lubricant-infused materials", Science 357, pp. 668-673, (2017).

Wong et al., "Bioinspired self-repairing slippery surfaces with pressure-stable omniphobicity", Nature Letter 2011, 477, pp. 443-447, 2011.

Wang et al., "Viscoelastic solid-repellent coatings for extreme water saving and global sanitation," Nature Sustainability, vol. 2, Dec. 2019, pp. 1097-1105.

* cited by examiner

FORMULATIONS AND PROCESSES TO GENERATE REPELLENT SURFACES ON MEDICAL DEVICES

CROSS-REFERENCE TO RELATED APPLICATIONS

This application is a Divisional of pending application Ser. No. 17/020,409, filed 14 Sep. 2020, which claims the benefit of U.S. Provisional Application No. 62/900,207 filed 13 Sep. 2019, U.S. Provisional Application No. 62/935,887 filed on 15 Nov. 2019 and U.S. Provisional Application No. 62/992,589 filed 20 Mar. 2020, the entire disclosures of each of which are hereby incorporated by reference herein.

STATEMENT REGARDING FEDERALLY SPONSORED RESEARCH

This invention was made with government support under Contract No. 2026140 awarded by the National Science Foundation. The government has certain rights in the invention.

TECHNICAL FIELD

The present invention relates to formulations and use thereof to form repellent coatings on surfaces of substrates including surfaces of medical devices.

BACKGROUND

Several patent applications disclose repellent and antibiofouling surfaces including, for example, WO 2019/222007, US 2019/0016903, and WO 2018/094161 to Wong et al., WO 2013/106588 to Ingber et al., US 2018/0187022 to Aizenberg et al. An article to Wang et al. also discloses repellent surfaces that have been developed with modified surfaces for fluid and solid repellency. See, Wang et al. Covalently Attached Liquids: Instant Omniphobic Surfaces with Unprecedented Repellency. Angewandte Chemie International Edition 55, 244-248 (2016).

However, it remains a challenge to develop a simple scalable process to form slippery surfaces over a wide variety of substrate materials.

SUMMARY OF THE DISCLOSURE

Advantages of the present disclosure include formulations and processes to prepare repellent coatings for a wide range of solid surfaces including those composed of one or more polymers, ceramics, glasses, metals, alloys, composites or combinations thereof. The formulations of the present disclosure can include reactive components and lubricant together in a single formulation (all-in-one formulation) and can advantageously be used to prepare repellent coated surfaces by a simple, one-step process. The repellent coatings can be formed on wide variety of fixtures and devices such as ceramic or metal plumbing fixtures, surfaces of glass substrates including mirrors, windshields, windows, medical devices such as ostomy appliances, etc. The formed repellent coatings are slippery and can repel and reduce adhesion to liquids, bacteria, mineral deposits, ice, frost, and viscoelastic materials (e.g., viscoelastic semi-solids and solids).

These and other advantages are satisfied, at least in part, by a formulation comprising: (i) one or more reactive components that can form a bonded layer on a surface in which the bonded layer comprises an array of compounds having one end bound to a surface and an opposite end extending away from the surface; (ii) an optional catalyst; (iii) a solvent; and (iv) a lubricant.

In some embodiments, formulations of the present disclosure can include, for example, low molecular weight silanes or siloxanes that have one or more hydrolysable groups. Such silanes or siloxanes can have a molecular weight of less than about 1,500 g/mol such as less than about 1,000 g/mol and can include, for example, alkoxysilanes, di-alkoxy silanes, tri-alkoxy silanes or combinations thereof. In certain embodiments, the array of compounds and/or polymers formed from the reactive compounds are not crosslinked along the chains thereof. In still further embodiments, relative amounts of the one or more reactive components to lubricant by weight in the formulation comprises 1 part reactive components to about 0.01 to about 1 parts lubricant. Catalysts can include acid catalysts such as sulfuric acid, hydrochloric acid, acetic acid, phosphoric acid, nitric, or combinations thereof. Solvents can include a lower ketone, a lower alcohol, a lower ether, a lower ester, a lower halogenated solvent and combinations thereof. Lubricants can include a silicone oil or a mineral oil or a plant oil or any combination thereof. Other components can be included in the formulations of the present disclosure such as a fragrance.

An additional advantage of the present disclosure includes a process of forming a repellent coating on a surface from the formulations disclosed herein. The process includes drying a formulation disclosed herein on a surface of a substrate to substantially remove the solvent and to form a bonded layer on the surface with the lubricant stably adhered to the bonded layer. Advantageously, the formed bonded layer comprises an array of compounds each having one end bound to the surface and an opposite end extending away from the surface. The process can also comprise a step of applying the formulation to a substrate surface prior to drying the formulation on the surface. By such a process, multiple steps of forming a repellent coating can be avoided, e.g., the multiple steps of first forming a bonded layer followed a step of applying a lubricant layer to a preformed bonded layer.

In some embodiments, processes of forming a repellant coating on a substrate from formulations disclosed herein includes drying the formulation on a surface composed of a glass, a ceramic or a polymer of a substrate to substantially remove the solvent and to form a bonded layer on the surface with the lubricant stably adhered to the bonded layer. The one or more reactive components can form a bonded layer by covalently bonding to the surface forming an array of compounds each compound having one end bound to the surface and an opposite end extending away from the surface. The repellent coating can be formed on wide variety of fixtures and devices such as ceramic or metal plumbing fixtures, surfaces of glass substrates including mirrors, windshields, windows, medical devices such as ostomy appliances, etc.

Process of the present disclosure can further include forming a coupling layer on substrate surfaces, e.g., substrate surfaces composed of one or more polymers, to couple the repellent coating to the substrate surface. Such coupling layers include functional groups, e.g., hydroxyl, ester or acid pendant groups, that can react with the reactive components of the formulations of the present disclosure.

Process of the present disclosure can further include applying the formulation on the surface of the substrate. Advantageously, applying the formulation and/or drying can be carried out in air and/or at atmospheric pressure.

In some embodiments, the formulation applied to a surface of a substrate to form a repellent coating thereon can comprise: (i) one or more reactive components, (ii) an acid catalyst, (ii) a solvent, and (iv) a lubricant having a viscosity of from 2 cSt to 1000 cSt as measured at 25° C.

Another advantage of the present disclosure includes substrates having a repellent coating thereon. Such substrates can include those composed of one or more polymers, ceramics, glasses, metals, alloys, composites or combinations thereof. The repellent coatings of the present disclosure can be formed on medical devices including medical devices having surfaces composed of one or more polymeric components such as on one or more surfaces of ostomy appliances. Advantageously, the repellent coating includes a bonded layer on the surface of a substrate comprising an array of compounds each having one end bound to the surface and an opposite end extending away from the surface.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

DETAILED DESCRIPTION OF THE DISCLOSURE

Figure 1:
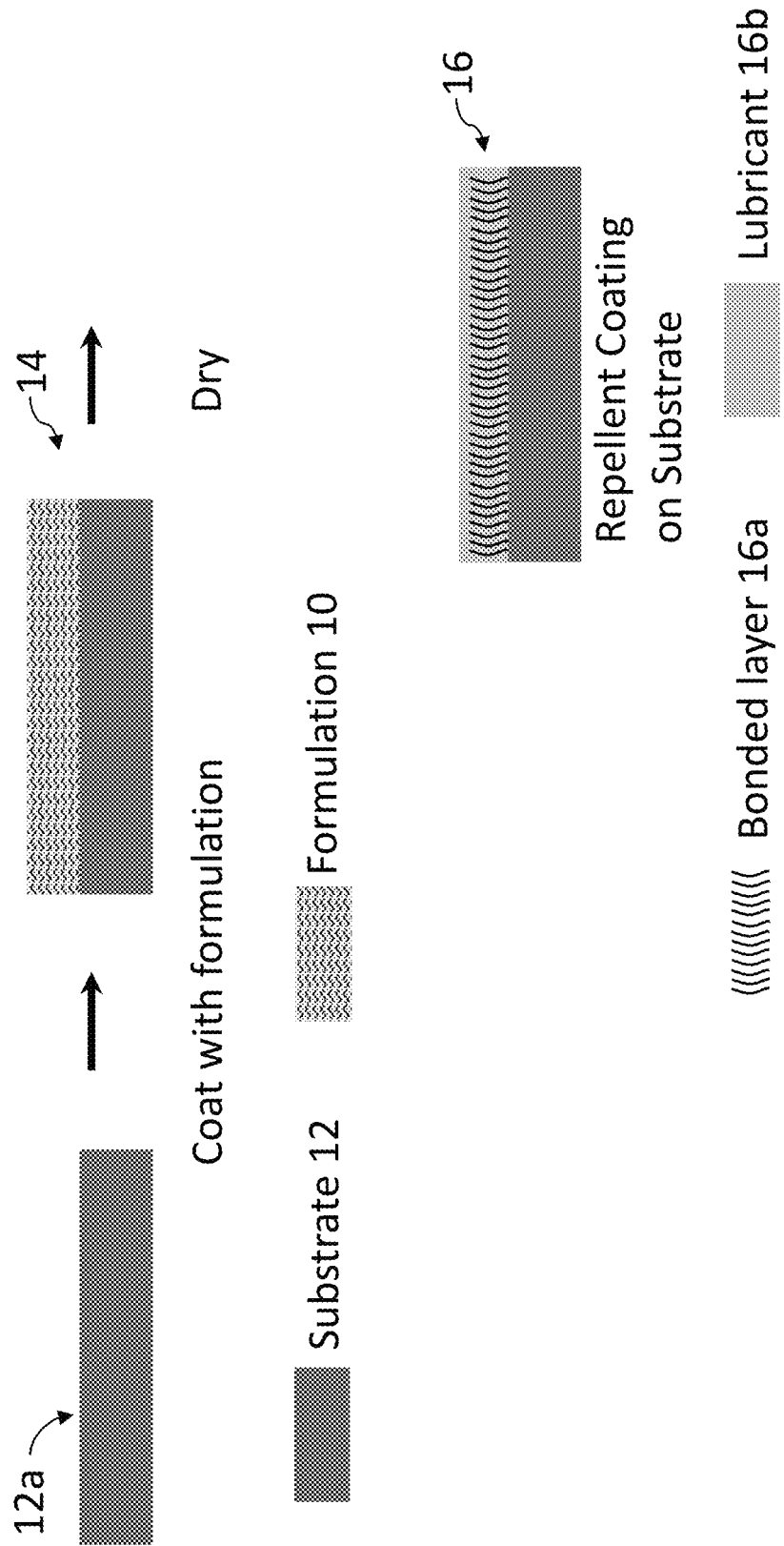
FIG. 1 is schematic illustrating the preparation of a repellent coating in accordance with the present disclosure.

The present disclosure relates to formulations that can greatly simplify and can reduce fabrication time, the number of steps, and costs associated with the formation of a repellent coating system. The repellent coating systems that can be formed by formulations of the present disclosure include a system of a lubricant layer infused into a bonded layer. Typically, preparing such a repellent coating system required separate steps of preparing one or more layers bound to a surface, followed by the steps of cleaning the formed bonded layer and then applying a lubricant layer to the cleaned bonded layer. It was not expected that an all-in-one formulation could be used to prepare a repellent coating system comprising a bonded layer with an infused lubricant layer given that the lubricant could interfere with the reactive components forming a bonded layer or not properly form an infused layer with the bonded layer. It was further not expected that the conventional practice of cleaning a formed bonded layer prior to applying a lubricant could be avoided. However, formulations of the present disclosure can advantageously form a repellent coating system of a stably adhered lubricant layer in a bonded layer without the need for separate steps by use of a single formulation that includes components to fully form the repellent coating system.

Such a formulation includes: (i) reactive component(s) to form the bonded layer on a surface of a substrate; (ii) optional catalyst(s); (iii) solvent(s); and (iv) lubricant(s). The reactive component(s) of the formulation are used to form a bonded layer onto the surface of a substrate by allowing them to react with the surface to form an array of compounds on the surface in which each compound has one end covalently bound to the surface and an opposite end extending away from the surface. As such, the bonded layer resembles a brush with linear chains bound to the surface. The lubricant of the formulation is stably adhered to the bonded layer primarily through van der Waals interactions to form a repellent coating system (herein after repellent coating) on the surface. A catalyst can facilitate and accelerate formation of the bonding layer at a reduced time and temperature and the solvent can also facilitate formation of the bonding layer and entrenchment of the lubricant within the bonding layer.

The bonded layer can be formed directly or indirectly on a surface of a substrate by reacting the reactive components of the formulation with functional groups, e.g. hydroxyl groups, acid groups, ester groups, etc., on the surface of the substrate. Such functional groups can be naturally present or induced on the substrate such as by treating the surface with oxygen plasma or by heating under the presence of air or oxygen, etc. A coupling layer can be formed on substrate surfaces, e.g., substrate surfaces composed of one or more polymers, to couple the repellent coating to the substrate surface. Such coupling layers include functional groups, e.g., hydroxyl, ester or acid pendent groups, that can react with the reactive components of the formulations of the present disclosure and include, for example, a silica or silicon dioxide layer, a metal oxide layer such as titanium dioxide, aluminum oxide, a polymeric layer having hydroxyl, ester or acid pendant groups such as a poly(vinyl alcohol) (PVA) or copolymer thereof, a poly(vinyl acetate) (PVAc), or copolymer thereof such as poly (ethylene-vinyl acetate) (PEVA), a polyacrylic or copolymer thereof, a polyphenol such as tannic acid, epigallocatechin gallate, epicatechin gallate, epigallocatechin, raspberry ellagitannin, theaflavin-3-gallate, tellimagrandin II, etc. The coupling layer advantageous can be formed on the surface of the substrate by solution coating, by applying the coupling layer as a melt, or by bonding a coupling layer in the form of a film onto a substrate through methods such as ultrasonic welding, hotplate welding, vibration welding, solvent bonding, UV bonding, roll bonding, and adhesive bonding. The coupling layer can have a thickness of less than about 1 mm such as less than 100 μm or less than about 50 μm or 10 μm and even less than 1 μm such as less than 500 nm, etc. or between and including such values.

Useful reactive components for formulations of the present disclosure include, for example, reactive components that have one end that bonds to the substrate surface, e.g., covalently bonds to reactive groups on the surface, to form an assembly of compounds. Such reactive components preferably have a chain length of at least 3 carbons. Other useful reactive components include polymerizable monomers that can react to form an array of linear polymers having ends anchored to the surface and opposite ends extending away from the surface. To increase the speed of forming a coating the reactive components of the formulation are selected to undergo a condensation reaction with loss of a small molecule such as water, an alcohol, which can be readily removed to drive the reaction to more or less completion under ambient temperatures and pressures. Preferably the linear polymers, with one end attached to the surface and the other extending away from the surface, do not form covalent bonds or crosslink with the adjacent linear polymers (e.g., forms brush-like structures). A lack of crosslinking allows the chains and ends extending away from the surface higher mobility in the adhered lubricant of the repellent coating system.

Useful reactive components for formulations of the present disclosure include, for example, low molecular weight silanes or siloxanes that have one or more hydrolysable groups. Such silanes or siloxanes have a molecular weight of less than about 1,500 g/mol such as less than about 1,000 g/mol and include a monoalkyl or mono-fluoroalkyl phosphonic acid such as 1H,1H,2H,2H-perfluorooctane phosphonic acid, an alkoxysilane such as a mono-alkoxy silane, e.g., an alkyl, fluoroalkyl and perfluoroalkyl mono-alkoxy silane, trimethylmethoxysilane; a di-alkoxy silane, e.g., a dialkyl di-alkoxy silane, such as a $C_{1-8}$ dialkyldialkoxy silane e.g., dimethyldimethoxysilane, dimethoxy(methyl)octylsilane, a di-alkoxy, diphenyl silane, diethyldiethoxysilane, diisopropyldimethoxysilane, di-n-butyldimethoxysilane, diisobutyldimethoxysilane, diisobutyldiethoxysilane, isobutylisopropyldimethoxysilane, dicyclopentyldimethoxysilane, a di-alkoxy, fluoroalkyl or perfluorosilane, dimethoxy-methyl(3,3,3-trifluoropropyl)silane, (3,3,3-trifluoropropyl)methyldimethoxysilane, a alkyltrimethoxysilane, a tri-alkoxy silane, e.g., a perfluoroalkyl-tri-alkoxy silane, trimethoxy(3,3,3-trifluoropropyl)silane, trimethoxymethylsilane, 1H,1H,2H,2H-perfluorodecyltrimethoxysilane, 1H,1H,2H,2H-perfluorodecyltriethoxysilane, nonafluorohexyltrimethoxysilane, nonafluorohexyltriethoxysilane, (tridecafluoro-1,1,2,2-tetrahydrooctyl)trimethoxysilane, tridecafluoro-1,1,2,2-tetrahydrooctyl)triethoxysilane, heptadecafluoro-1,1,2,2-tetrahydrodecyl)trimethoxysilane, (heptadecafluoro-1,1,2,2-tetrahydrodecyl)triethoxysilane, a chlorosilane, e.g., octyldimethylchlorosilane, a dichlorosilane, e.g., diethyldichlorosilane, di-n-butyldichlorosilane, diisopropyldichlorosilane, dicyclopentyldichlorosilane, di-n-hexyldichlorosilane, dicyclohexyldichlorosilane, di-n-octyldichlorosilane, 3,3,3-trifluoropropyl)methyldichlorosilane, nonafluorohexylmethyldichlorosilane, (tridecafluoro-1,1,2,2-tetrahydrooctyl)methyldichlorosilane, (heptadecafluoro-1,1,2,2-tetrahydrodecyl)methyldichlorosilane, (3,3,3-trifluoropropyl)dimethylchlorosilane, nonafluorohexyldimethylchlorosilane, tridecafluoro-1,1,2,2-tetrahydrooctyl)dimethylchlorosilane, (heptadecafluoro-1,1,2,2-tetrahydrodecyl)dimethylchlorosilane, a trichlorosilane, e.g., (tridecafluoro-1,1,2,2-tetrahydrooctyl)trichlorosilane, (3,3,3-trifluoropropyl)trichlorosilane, nonafluorohexyltrichlorosilane, (heptadecafluoro-1,1,2,2-tetrahydrodecyl)trichlorosilane, an amino silane, e.g., nonafluorohexyltris(dimethyamino)silane, etc.

The alkoxy groups of such reactive components can be $C_{1-4}$ alkoxy groups such as methoxy (—OCH$_3$), ethoxy (—OCH$_2$CH$_3$) groups and the alkyl groups of such reactive components can have various chain lengths, e.g., of $C_{1-30}$, such as $C_{3-30}$. The alkyl groups of such reactive components that form linear polymers generally have a lower alkyl group, e.g., $C_{1-16}$, such as $C_{1-8}$. The alkyl groups in each case can be substituted with one or more fluoro groups forming fluoroalkyl and perfluoroalkyl groups of $C_{1-30}$, $C_{3-30}$, $C_{1-16}$, $C_{1-8}$, etc. chains such as a fluoroalkyl or perfluoroalkyl alkoxysilane, a difluoroalkyl or diperfluoroalkyl di-alkoxy silane, a fluoralkyl or perfluoralkyl tri-alkoxy silane having such chain lengths.

The bonded layer can be formed from the formulation by reacting the reactive components of the formulations directly with exposed hydroxyl groups or other reactive groups on the surface of a substrate to form an array of linear compounds having one end covalently bound directly to the surface through the hydroxyl groups or other reactive groups on the surface of a substrate. Alternatively, the bonded layer can be formed by polymerizing one or more of a silane monomer directly from exposed hydroxyl groups or other reactive groups on the surface of a substrate to form an array of linear polysilanes or polysiloxanes or a combination thereof covalently bound directly to the surface through the hydroxyl groups or other reactive groups on the surface of a substrate. Preferably the linear polymers, with one end attached to the surface and the other extending away from the surface, do not form covalent bonds or crosslink with the neighboring linear polymers (e.g., forms brush-like structures).

The bonded layer can have a thickness of less than about 1000 nm. In some cases, the thickness of the bonded layer can be less than about 500 nm, less than about 100 nm or even less than about 10 nm, e.g. from about 1 or 5 nm to about 500 nm.

One or more catalysts can be included in the formulations of the present disclosure. As used herein catalysts references to one or more catalysts. A catalyst can facilitate and accelerate formation of the bonding layer. Useful catalysts that can be included in the formulation include acid catalysts such as sulfuric acid, hydrochloric acid, acetic acid, phosphoric acid, nitric acid, or combinations thereof. In some embodiments, the catalyst does not include a catalyst containing a transition metal such as platinum since such catalysts tend to increase costs and remain in a formed coating including such catalysts.

The formulation of the present disclosure also includes a solvent or medium which can be a single solvent or multiple solvents such as a solvent system, collectively referred to herein as a solvent. A solvent can facilitate formation of the bonding layer and the infusion of the lubricant within the bonding layer during formation of the repellent coating on the surface. Preferably, the solvent should have a relatively low boiling point and relatively high vapor pressure for ease of evaporating the solvent from the formulation when forming the repellent coating therefrom. In an embodiment, the solvent of formulations of the present disclosure can have a boiling point at atmospheric pressure of no more than about 140° C., such as no more than about 82.5° C. and even no more than about 60° C. In other embodiments, the solvent of formulations of the present disclosure can have a vapor pressure of 4.3 kPa at 20° C., such as isopropyl alcohol. Solvents with higher boiling points and lower vapor pressure can be used but tend to inhibit the rate of drying and/or may need to be removed by application of a reduced atmosphere to remove the solvent.

Useful solvents that can be included in the formulation of the present disclosure can include one or more of a lower ketone, e.g., a $C_{1-8}$ ketone such as acetone, methylethyl ketone, cyclohexanone, a lower alcohol, e.g., a $C_{1-8}$ alcohol such as methanol, ethanol, isopropanol, a butanol, a lower ether, e.g., a $C_{1-8}$ ether such as dimethyl ether, diethyl ether, tetrahydrofuran, a lower ester, e.g., a $C_{1-8}$ ester such as ethyl acetate, butyl acetate, glycol ether esters, a lower halogenated solvent, e.g., a chlorinated $C_{1-8}$ such as methylene chloride, chloroform, an aliphatic or aromatic hydrocarbon solvent such as hexane, cyclohexane, toluene, xylene, dimethylformamide, dimethyl sulfoxide and any combination thereof. A solvent can also include a certain amount of water, e.g., less than about 5 wt % of water.

The formulation of the present disclosure also includes a lubricant or combination of lubricants, collectively referred to herein as a lubricant. To form a stably adhered lubricant to a bonded layer which in turn is formed from the reactive components of the formulation, a lubricant should have strong affinity to the bonded layer and/or the substrate so that the lubricant can fully wet the surface (e.g., result in an equilibrium contact angle of less than about 5°, such as less than about 3°, about 2°, about 1°) and stably adhere on the surface. Further since solvent is removed in forming the repellent coating from the formulation and the lubricant is intended to adhered to the bonding layer, the lubricant should have a boiling point that is significantly higher than the boiling point of the solvent, e.g., the boiling point of the lubricant should be at least 10° C. higher than the solvent under the same atmospheric pressure, such as at least 20° C., 40° C., 60° C., 80° C., 100° C., 120° C., 150° C., 200° C., 250° C., etc. higher than the solvent under the same atmospheric pressure. In addition, the lubricant should be mobile in the formed repellent coating and thus it is preferably that the lubricant not substantially react, if at all, with the reactive components in the formulation. A stably adhered lubricant to the bonded layer is believed due primarily to van der Waals forces, not through covalent boding to the bonding layer. In certain embodiments, lubricants for the present disclosure do not have groups that would react with the reactive components of the formulation.

Further, a stably adherent lubricant is distinct from a lubricant placed on a surface, or modified surface, that does not wet the surface (e.g. forms an equilibrium contact angle of greater than 10°) and/or simply slides off the surface within minutes or shorter periods when the surface is raised to a sliding angle of up to 90°. A lubricant stably adhered to a bonded layer is one that substantially remains (greater than about 80%) on bonded layer for at least one hour, or longer periods such as several hours and days and months, even when the surface substrate is at a 90° from horizontal.

A lubricant useful for formulations of the present disclosure should have a sufficient viscosity yet be relatively mobile to facilitate repellence of the coating system at temperatures intended for use with the substrate having the repellent coating. Such temperatures can range from about −30° C. to about 300° C. As such, a lubricant should preferably have a viscosity of at least about 1 cSt (as measured at 25° C.) such as at least about 2 cSt, 3 cSt, 4 cSt, 5 cSt, 6 cSt, 7 cSt, 8 cSt, 9 cSt, 10 cSt, 15 cSt, 20 cSt, 30 cSt, etc. (as measured at 25° C.) and any value therebetween. Further, so that the lubricant can be mobile at certain temperatures in which the repellent coating can be used, a lubricant should preferably have a viscosity of no more than about 1500 cSt as measured at 25° C., such as no more than about 950 cSt, 900 cSt, 850 cSt, etc., as measured at 25° C., and any value therebetween. In an embodiment, a lubricant for a formulation of the present disclosure can have viscosity ranging from about 1 cSt to about 1500 cSt, such as from about 2 cSt, 3 cSt, 4 cSt, 5 cSt, 6 cSt, 7 cSt, 8 cSt, 9 cSt, 10 cSt, 15 cSt, 20 cSt, 30 cSt, etc. to about 1500 cSt, 1200 cSt, 1000 cSt, 800 cSt, 350 cSt, 200 cSt, 150 cSt, etc., as measured at 25° C., and any value therebetween. For high temperature uses, the repellent coating can have a lubricant with an even higher viscosity at room temperature since the viscosity of such a lubricant would be less at the higher use temperature. Further, lubricant densities of less than about 2 g/cm$^3$ would be preferable at temperature range from 15° C. to 25° C.

A lubricant included in the formulation of the present disclosure can be one or more of an omniphobic lubricant, a hydrophobic lubricant and/or a hydrophilic lubricant. The lubricant can include a perfluorinated oil or a silicone oil or a hydroxy polydimethylsiloxane (PDMS) or a plant oil. Other lubricants that can be used include perfluoropolyether, perfluoroalkylamine, perfluoroalkylsulfide, perfluoroalkylsulfoxide, perfluoroalkylether, perfluorocycloether oils and perfluoroalkylphosphine and perfluoroalkylphosphineoxide oils as well as mixtures thereof. Preferable, the lubricant is chosen to have a strong chemical affinity to the particular bonding layer and/or substrate so that the lubricant can fully wet and stably adhere to the surface via the boding layer. For example, perfluorinated oils such as a perfluoropolyether (e.g., Krytox oil) can fully wet and stably adhere to a polymeric siloxane and/or silane bonding layer including fluorinated alkyl silanes such as perfluorinated alkyl silanes. Such a bonding layer can be formed from reactive fluoroalkyl silanes in a formulation that reacts with functional groups on a surface of a substrate. Silicone oil or plant oil can fully wet and stably adhere to a bonded layer comprised of an array of linear polydimethylsiloxane (PDMS), for example. Hydroxy PDMS can also fully wet and stably adhere to a bonded layer comprised of an array of linear polydimethylsiloxane (PDMS), for example. Such a PDMS bonding layer can be formed from polymerizing dimethyldimethoxysilane from a surface of a substrate. Mineral oils or plant oils can fully wet and stably adhere to a bonding layer including an array of alkyl silanes which can be formed from alkyltrichlorosilanes or alkyltrimethoxysilanes. The alkyl groups on such alkylsilanes can have various chain lengths, e.g., alkyl chains of $C_{1-30}$. Other lubricants that will be compatible with alkylsilanes with various chain lengths and polysiloxanes polymerized from one or more dialkyldialkoxysilanes such as dimethyldimethoxysilane include alkane oils, and plant oils such as a vegetable oil, avocado oil, algae extract oil, olive oil, palm oil, soybean oil, canola oil, castor oil, rapeseed oil, corn oil, peanut oil, coconut oil, cottonseed oil, palm oil, safflower oil, sesame oil, sunflower seed oil, almond oil, cashew oil, hazelnut oil, macadamia oil, Mongongo nut oil, pecan oil, pine nut oil, peanut oil, walnut oil, grapefruit seed oil, lemon oil, orange oil, amaranth oil, apple seed oil, argan oil, avocado oil, babassu oil, ben oil, borneo tallow nut oil, cape chestnut oil, carob pod oil, camellia seed oil, cocoa butter, cocklebur oil, cohune oil, grape seed oil, Kapok seed oil, Kenaf seed oil, Lallemantia oil, Marula oil, Meadowfoam seed oil, macadamia nut oil, mustard oil, Okra seed oil, papaya seed oil, Pequi oil, poppyseed oil, pracaxi oil, prune kernel oil, quinoa oil, ramtil oil, rice bran oil, rapeseed oil, sesame oil, safflower oil, Sapote oil, Shea butter, squalene, soybean oil, tea seed oil, tigemut oil, tomato seed oil, liquid terpenes (e.g., Citropol®), and other similar plant-based oils etc. The plant-based oils can be used alone or with other lubricants or as a mixture of plant-based oils alone or with other lubricants.

Other components can be included in the formulations of the present disclosure such as a fragrance, i.e., a substance that emits a pleasant odor. Such a fragrance includes, for example, a natural or synthetic aroma compound or an essential oil such as a lemon oil, bergamot oil, lemongrass oil, orange oil, coconut oil, peppermint, oil, pine oil, rose oil, lavender oil or any combination of the foregoing. As an example, the fragrance added to the formulation of the present disclosure can have a smell of lemon, or rose, or lavender, or coconut, or orange, or apple, or wood, or peppermint, etc. One or more fragrance can be added to a formulation of the present disclosure as is, e.g., without dilution, and can be added in a range of about 0.0005 parts to about 10 parts, e.g. from about 0.01 to about 5 parts, by weight in place of the solvent. In certain aspects, the fragrance is soluble in alcohols and siloxanes.

In certain embodiments, the concentrations of various components on a weight bases in formulations of the present disclosure can include the ranges provided in the tables below:

Relative ratio of reactive components to lubricant(s) in formulation

| Component by weight | 1st range (from about to about) | 2nd range (from about to about) | 3rd range (from about to about) |
|---|---|---|---|
| parts reactive components | 1 | 1 | 1 |
| parts lubricant | 0.001-50 | 0.005-10 | 0.01-1 |

Relative ratio of reactive components to acid catalyst

| Component by weight | 1st range (from about to about) | 2nd range (from about to about) | 3rd range from about to about) |
|---|---|---|---|
| parts reactive components | 1 | 1 | 1 |
| parts catalyst | 0.01-1 | 0.05-0.5 | 0.08-0.12 |

Relative ratio of components in formulation

| Component by weight | 1st range (from about to about) | 2nd range (from about to about) | 3rd range (from about to about) |
|---|---|---|---|
| parts reactive components | 1 | 1 | 1 |
| parts lubricant | 0.0005-10 | 0.005-2.5 | 0.01-1 |
| parts acid catalyst | 0.01-1 | 0.05-0.5 | 0.08-0.12 |
| solvent | 5-200 | 8-100 | 10-20 |

For some embodiments of formulations of the present disclosure, the lubricant concentration is no more than about 50 wt %, such as from about 0.05 wt % to about 50 wt %. Lubricant concentrations larger than 99 wt % tend inhibit formation of the repellent coating system on the surface.

In an aspect of the present disclosure, a repellent coating system can be formed from a fluorinated alkyl silane and/or a fluorinated lubricant onto a substrate. For example, one or more $C_2$-$C_8$ fluorinated alkyl silane reactive components (e.g., about 2 wt % to about 10 wt %) can be combined in an all-in-one formulation with one or more perfluoropolyether lubricants (e.g., about 0.02 wt % to about 10 wt %), catalyst and solvent. Such a formulation can be applied onto a glass substrate, for example.

Advantageously, the formulation of the present disclosure can have a long shelf-life without substantial deactivation of the reactive components when stored around room condition in closed containers. The formulations of the present disclosure can then be readily used to prepare repellent coating.

Repellent coatings prepared from formulations of the present disclosure can repel a broad range of liquids and solids including but not limited to rain water, soapy water, hard water, blood, bacteria, etc. with a typical contact angle hysteresis of less than about 10°. The repellent coatings can also repel viscoelastic solids having a dynamic viscosity of at least $1 \times 10^{-3}$ Pa·s, such as at least 1 Pa·s, 100 Pa·s, 10,000 Pa·s, to 100,000 Pa·s.

In practicing certain aspects of the present disclosure, it is preferable to form a repellent coating on a substrate with a relatively smooth surface. In some embodiments, the substrate surface has an average roughness (Ra) at a microscale level, e.g., Ra of less than a few microns, and preferably less than a few hundred nanometers, or even less than a few nanometers. Advantageously, the surface of a substrate to which a repellent coating is to be formed thereon is relatively smooth, e.g., the surface has an average roughness Ra of less than about 4 μm, e.g., less than about 2 μm and less than about 1 μm average surface roughness and even less than about 500 nm, e.g., less than about 100 nm, 80 nm, 60 nm, 40 nm 20 nm, 10 nm, etc. average surface roughness.

Average surface roughness can be measured by atomic force microscope (AFM) using tapping mode with a scanning area of 2×2 μm² for measuring average surface roughness in a 0.1-nanometer scale or equivalent technique. Average surface roughness can be measured by Zygo optical profilometer with an area of 475×475 μm² for measuring average surface roughness in a 1-nanometer scale or equivalent technique.

In practicing certain aspects of the present disclosure, substrates having a smooth surface that can be used in the present disclosure include those composed of one or more polymers, such as polycarbonate, polypropylene, high density polyethylene, polyvinyl chloride, polyurethane, poly (methyl methacrylate), silicone, nylon, poly(ethylene-vinyl acetate), polyvinyl acetate, polyvinyl alcohol, architecture/construction materials such marble, granite, stone, terracotta, brick, asphalt, cement, ceramics, china, porcelain, glass, metals such as titanium, copper, aluminum, carbon steel, etc., metal alloys, cellulose such as wood, paper, cottons, other materials found in solid form, etc. and combinations thereof. The surface of the substrate can be treated to form reactive groups such as hydroxyl groups, such as by oxygen plasma treatment, or by heating under the presence of air or oxygen (for the case of metals). The substrate can include a reactive coupling layer and the repellent coating formed on the surface of the coupling layer.

The substrate surface can be cleaned and dried before applying a formulation. One example for the cleaning a substrate surface involves the use of a lower alcohol, e.g., ethanol or isopropanol, to rinse the surface. Then the surface can be dried and the formulation applied.

Processes for preparing a repellent coating on a surface of a substrate includes drying a formulation of the present disclosure on a surface of a substrate to substantially remove the solvent, e.g., greater than about 60%, 65%, 70%, 80%, 85%, 90%, 95% by weight and higher of the solvent can be removed in the drying step. Drying the formulation concentrates the reactive components and causes them to react to form a bonded layer on the surface of the substrate. The reactive components are chosen such that they react with the surface to form an array of compounds each having one end bound to the surface and an opposite end extending away from the surface. Drying the formulation also causes the lubricant to be concentrated and retained within the bonded layer. The lubricant is thus chosen to have an affinity for the bonded layer and/or surface so that it can stably adhered to the surface via the bonded layer.

Repellent coatings on a surface of a substrate can advantageously be formed by drying under relatively low temperatures, e.g., temperatures ranging from about 0° C. to about 80° C. Hence, forming the repellent coating from formulations of the present disclosure can be carried out at from about 5° C. to about room temperature, e.g., 20° C., and at elevated temperature, e.g., greater than about 25° C., 30° C., 40° C., 50° C., 55° C., 60° C., 70° C., 80° C., etc. Forming the repellent coating can also be advantageously carried out in a relatively short period of time such as in a period of no more than about 120 minutes such as 60 minutes, e.g., no more than about 30 minutes and even as short a period of no more than about 5 minutes. Although a vacuum could accelerate drying of the formulation, it is not necessary for the process and drying of formulations of the present disclosure can be carried out at atmospheric pressure, e.g., at about 1 atm. Further, drying and/or applying the formulation of the present disclosure can be carried out in air or in an inert atmosphere, e.g., a nitrogen atmosphere.

Applying formulations of the present disclosure on to a surface of a substrate can be carried-out with liquid-phase processing thereby avoiding complex equipment and processing conditions. Such liquid-phase processing includes, for example, simply submerging the substrate (dip-coating) or applying the formulation on to the substrate surface by wiping, spraying (including aerosol spray), curtain coating and/or spin coating the formulation on to the surface. Other methods of applying formulations of the present disclosure on to a surface of a substrate can be carried out by wiping a towel made of a fabric, paper or similar material, or a sponge or squeegee, infused with the formulation, on the surface to transfer the formulation from the towel, sponge, squeegee to the surface of the substrate. Advantageously, the formulation can be applied to the substrate surface under ambient temperatures and/or atmospheric pressures and in air, e.g., formulations of the present disclosure can be applied on surfaces of substrates in air and at atmospheric pressure. In certain embodiments, the formation of the bonded layer is accelerated in the presence of a catalyst, e.g., an acid catalyst, and water. The water can be either available from the solvent or from the atmosphere or both. Drying the formulation in an atmosphere having some moisture, e.g., an ambient humidity of at least about 10% at 20° C. and atmospheric pressure is preferable from certain of the reactive components. Hence in some embodiments, the formulation of the present disclosure is dried at an ambient humidity of from about 10% to no more than about 80%.

Forming the repellent coating by applying and drying a formulation of the present disclosure can be advantageously carried out in a relatively short period of time such as in a period of no more than about 120 minutes such as 60 minutes, e.g., no more than about 30 minutes and even as short a period of no more than about 5 minutes. Further, drying and/or applying the formulation of the present disclosure can be carried out in air or in an inert atmosphere, e.g., a nitrogen atmosphere, and at atmospheric pressure. Advantageously, the repellent coating can be formed on substrate surfaces under ambient conditions (e.g., in air under about one atmosphere of pressure and at temperatures from about 5° C. to about 35° C.).

FIG. 1 illustrates a process of forming a repellent coating on a surface of a substrate in accordance with an aspect of the present disclosure. For this example, a formulation (10) of the present disclosure is applied to a substrate (12) to form a substrate with the formulation coating on its surface (14). For this example, the substrate is a smooth substrate (e.g., a substrate with a surface having an average roughness of less than 1 μm). Drying the formulation on the surface of the substrate to substantially remove the solvent forms a repellent coating (16) in which a bonded layer (16a) is covalently bound to the surface (12a) with a lubricant layer (16b) infused in the bonded layer (16a). The bonded layer resembles a brush on the surface of the substrate with lubricant infused within the bonded layer.

Figure 2:
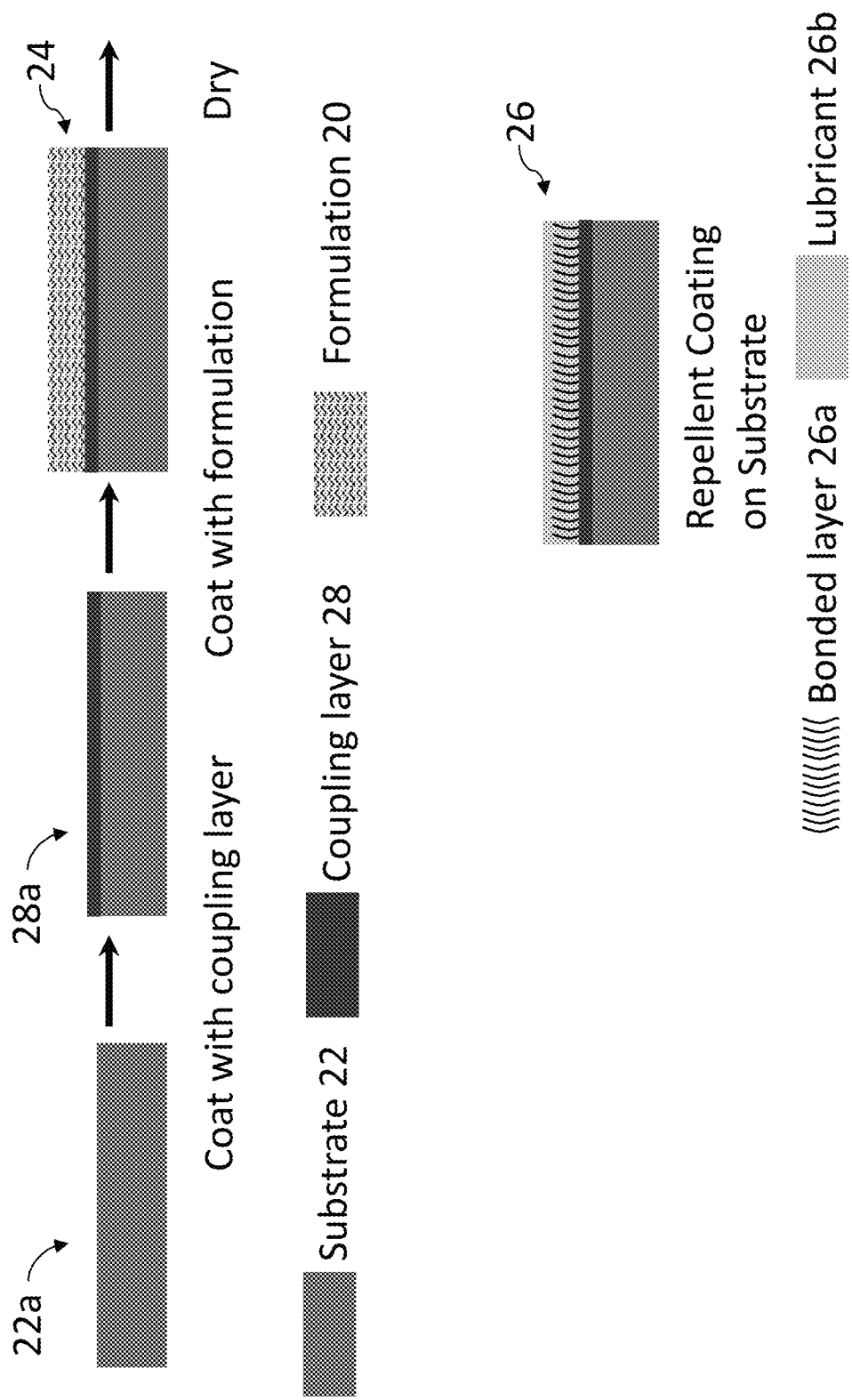
FIG. 2 is schematic showing the preparation of a repellent surface on substrates with a reactive coupling layer.

FIG. 2 illustrates another process of forming a repellent coating on a surface of a substrate in accordance with an aspect of the present disclosure. For this example, a coupling layer (28) is first applied to a surface (22a) of a substrate (22). Coupling layers are useful for substrates that have relatively inert surfaces such as many surfaces composed of polymeric components. A formulation (20) of the present disclosure is applied to a surface (28a) of the coupling layer (28) to form a substrate with the formulation coating on its surface (24). Drying the formulation on the surface to substantially remove the solvent forms a repellent coating (26) in which a bonded layer (26a) is covalently bound to the surface (28a) with a lubricant layer (26b) infused in the bonded layer (26a). The bonded layer resembles a brush on the surface of the substrate with lubricant infused within the bonded layer.

In some instances and under certain conditions, the lubricant of the repellent coating can be depleted over time. Advantageously, the lubricant can be replenished by applying lubricant, either the same or a different lubricant than used to prepare the repellent coating, to the bonded layer to renew the repellent coating system on the surface of the substrate.

An exemplary formulation of the present disclosure can include one or more polymerizable silane monomers and/or siloxane monomers as the reactive component. Drying such a formulation polymerizes the monomers from exposed hydroxyl groups on the surface to form an array of linear polysilanes or polysiloxanes or a combination thereof. By this technique, the array of linear polymers has ends covalently bound to the surface and opposite ends extending away from the surface and resemble a brush. Exemplary formulations with ranges for a polymerizable monomers, lubricant, solvent and acid catalyst is provided in Tables 1 and 2 below and with a fragrance in Table 3 below.

TABLE 1

Concentration ranges for an exemplary one-step coating formulation

| Component | Approximate Concentration Range |
| --- | --- |
| Silane monomers and/or Siloxane monomers | 4-15 wt % |
| Solvent | 34-95 wt % |
| Acid Catalyst | 0.5-1 wt % |
| Lubricant | 0.05-50 wt % |

TABLE 2

Concentration ranges for another exemplary one-step coating formulation

| Component | Approximate Concentration Range |
| --- | --- |
| Silane monomers and/or Siloxane monomers | 4.5-9.0 wt % |
| Solvent | 45.0-90 wt % |

TABLE 2-continued

Concentration ranges for another exemplary one-step coating formulation

| Component | Approximate Concentration Range |
|---|---|
| Acid Catalyst | 0.5-1 wt % |
| Lubricant | 0.05-50 wt % |

TABLE 3

Concentration ranges for an exemplary one-step coating formulation with fragrance

| Component | Approximate Concentration Range |
|---|---|
| Silane monomers and/or Siloxane monomers | 4-15 wt % |
| Solvent | 29-95 wt % |
| Acid Catalyst | 0.5-1 wt % |
| Lubricant | 0.05-50 wt % |
| Fragrance | 0.01-5 wt % |

A particular example formulation can include dimethyldimethoxysilane as the polymerizable silane monomer to make up from about 4 wt % to about 15 wt %, e.g., from about 4.5 wt % to about 9.0 wt %, of the formulation; the lubricant can be a silicone oil or a hydroxyl-terminated polydimethylsiloxane or a vegetable oil (e.g., soybean oil) to make up about 0.05 to about 50 wt % of the formulation. The viscosity of the silicone oil or hydroxyl-terminated polydimethylsiloxane or the vegetable oil can range from about 20 cSt to about 350 cSt at 25° C. For this particular example, the solvent can be a lower ketone, or alcohol, e.g., acetone, ethanol, isopropanol (or isopropyl alcohol), a lower chlorinated solvent, e.g., chloroform etc. and any combination of the foregoing and make up about 45.0 wt % to about 95.0 wt % of the formulation. For this particular example, sulfuric acid and/or hydrochloric acid or acetic acid or phosphoric acid can be used as a catalyst to make up about 0.5 wt % to about 1.0 wt % of the formulation.

To demonstrate the effectiveness of certain formulations for the present disclosure, smooth glass slides were cleaned by isopropanol followed by applying a formulation by wiping it on the slide. The glass slides were then allowed sit in ambient condition, 23° C., 60% relative humidity, atmospheric pressure, for 5 min. After drying, repellent coatings were formed on surfaces of the glass slides using formulations with varying concentrations components. All of the tested repellent coatings exhibited a low sliding angle (<10°) against 20 µL water droplets. Note that a smaller sliding angle represents a better liquid repellency of the coated surface for the particular liquid. Further, the lubricant was stable on the surface and did not dewet. The resulting coating can repel a broad range of liquids and solids including but not limited to rain water, soapy water, hard water, blood with a typical contact angle hysteresis <10°. The repellent coatings can also repel viscoelastic solids with dynamic viscosity of at least $1 \times 10^{-3}$ Pa·s, 1 Pa·s, 100 Pa·s, 10,000 Pa·s, to 100,000 Pa·s.

Advantageously, the formulations of the present disclosure can be applied to surfaces of ceramic or metal toilets, sinks, plumbing fixtures, surfaces of glass substrates including mirrors, windshields, windows in a building, a glass optical lens for a camera, surfaces composed of one or more polymers such as plastic sinks, toilets, surfaces of personal protective equipment such as gowns, face shields goggles, shoe covering and shoes and medical devices such as ostomy appliances, catheter, syringe, scalpel, endoscope lens, metal and plastics implants (e.g., orthopedic implants, dental implants, glaucoma implants), prostheses, etc; automobile parts such as windshields, camera lens, lamp and sensing casings, mud flaps, car bodies; airplane parts such as windshield, airplane wings and bodies; marine parts such as submerged devices, cables, ships and boats; outdoor and indoor signage, bus step enclosures.

Many medical devices can benefit from the formulations and repellent coatings of the present disclosure including medical devices composed of polymeric surfaces. For example, an ostomy appliance (bag or pouch as they are commonly referred) can include a collection pouch and one or more ports including one or more outlet ports. Such ostomy appliances have surfaces typically made of one or more polymers that can be coated with formulations of the present disclosure to form one or more repellent surfaces. In one aspect of the present disclosure, a surface of an ostomy appliance, e.g., an inner surface, can include a repellent coating by drying a formulation of the present disclosure on such a surface to substantially remove the solvent and to form a bonded layer on the surface with the lubricant stably adhered to the bonded layer.

In addition, surfaces composed on certain polymeric components which tend to be relatively inert and resistant to modification can also benefit from the formulations and repellent coatings of the present disclosure. For such surfaces, a coupling layer can be applied to the polymeric substrate and a repellent coating system of the present disclosure prepared on a surface of the coupling layer.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

The following example formulations (Example 1 to Example 5) below vary the concentration of the lubricant in the formulation while maintaining the other components constant relative to each other, i.e., the approximate weight ratio of solvent (wt %):silane monomer (wt %):catalyst (wt %)=100:10:1. For the formulation in Examples 1-5 below, the formulation were prepared by mixing the components inside a container for about 1 min by stirring either by vortex mixing or by magnetic stirrer. The formulations were allowed to stand at room temperature for about 2 min before use. The formulation is stable for at least 3 months after preparation.

For these experiments, smooth glass slides were used as substrates. The surface roughness of the glass slides were about less than 10 nm. The glass slides were cleaned by rinsing with isopropanol prior to application of the formulation. Formulations having the components and concentrations of examples 1-5 were applied to different glass slides by dip coating or spraying followed by wiping the formulation on to the glass slide.

Example 1: Low Lubricant Concentration Formulation 1

| Component | Approximate Concentration Range |
| --- | --- |
| Reactive Monomer: dimethyldimethoxysilane | 9.0 wt % |
| Solvent: isopropanol | 89.95 wt % |
| Catalyst: sulfuric acid | 1.0 wt % |
| Lubricant: silicone oil or vegetable oil | 0.05 wt % |

Example 2: Low-Medium Lubricant Concentration Formulation 2

| Component | Approximate Concentration Range |
| --- | --- |
| Reactive Monomer: dimethyldimethoxysilane | 9.0 wt % |
| Solvent: isopropanol | 89.0 wt % |
| Catalyst: sulfuric acid | 1.0 wt % |
| Lubricant: silicone oil or vegetable oil | 1.0 wt % |

Example 3: Medium Lubricant Concentration Formulation 3

| Component | Approximate Concentration Range |
| --- | --- |
| Reactive Monomer: dimethyldimethoxysilane | 8.1 wt % |
| Solvent: isopropanol | 81.0 wt % |
| Catalyst: sulfuric acid | 0.9 wt % |
| Lubricant: silicone oil or vegetable oil | 10.0 wt % |

Example 4: Medium-High Lubricant Concentration Formulation 4

| Component | Approximate Concentration Range |
| --- | --- |
| Reactive Monomer: dimethyldimethoxysilane | 7.2 wt % |
| Solvent: isopropanol | 72.0 wt % |
| Catalyst: sulfuric acid | 0.8 wt % |
| Lubricant: silicone oil or vegetable oil | 20.0 wt % |

Example 5: High Lubricant Concentration Formulation 5

| Component | Approximate Concentration Range |
| --- | --- |
| Reactive Monomer: dimethyldimethoxysilane | 4.5 wt % |
| Solvent: isopropanol alcohol | 45.0 wt % |
| Catalyst: sulfuric acid | 0.5 wt % |
| Lubricant: silicone oil or vegetable oil | 50.0 wt % |

After application of the formulation to a glass slide, the formulation was then dried under ambient condition (e.g., 23° C., 60% relative humidity, atmospheric pressure) for 5 min to form a repellent surface on the glass slides. Subjecting the formulations to these drying conditions resulted in the dimethyldimethoxysilane monomer polymerizing by an acid-catalyzed condensation process to form an array of linear polysiloxanes bound to the glass surface with the silicone oil stably entrenched within the polysiloxane polymers. The estimated thickness of the grafted PDMS layer on glass is about 1-4 nm according to X-ray photoelectron spectroscopy (XPS) analysis.

All of the formulations of Examples 1 through 5 generated repellent surfaces exhibiting a low sliding angle (<10°) against 20 µL water droplets. To measure the sliding angles, a water droplet of known volume (e.g., 20 µL) is placed onto the coated substrate. The substrate is subsequently tilted gradually from a horizontal position until the water droplet begins to slide off the substrate. The angle (formed between horizontal and the flat tilted substrate) at which the water droplet begins to slide is the sliding angle. Further the lubricant was stable on the surface and did not dewet.

The shelf-life of certain of the above Example formulations were determined to be stable for over 12 months. For example, certain formulations were prepared on and tested over 12 months after their preparation by coating glass and found the repellent coatings resulted in sliding angles of 10 degree or less, which were similar to the results for the formulations around the time they were prepared.

Sliding angles were measured by a tilting stage or a goniometer.

Figure 3:
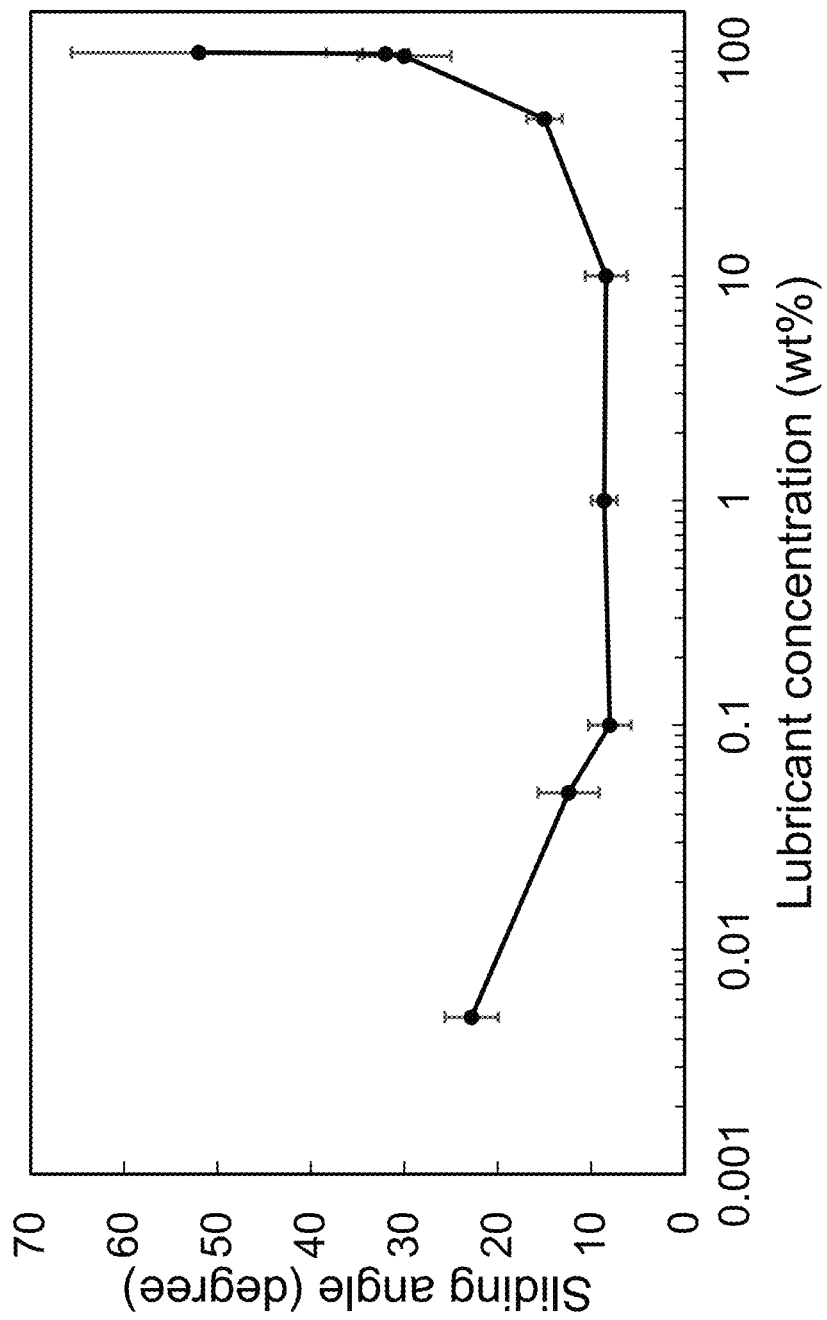
FIG. 3 is a chart showing water sliding angles versus lubricant concentrations for formulations including the lubricant in such concentrations that were used to form repellent coating in accordance with the present disclosure. The volume of the water droplets used was 20 μL.

FIG. 3 is a chart showing sliding angles versus lubricant concentrations for repellent surfaces prepared from formulations including formulations from Examples 1-5 above.

As seen from the data in FIG. 3, when the lubricant concentration is within the range of about 0.1 wt % to about 10 wt %, the sliding angle of a 20 µL droplet is smaller than 10 degrees. Note that the weight ratio of other components are constant, solvent (wt %):reactive monomers (wt %):catalyst (wt %)=100:10:1.

Figure 4:
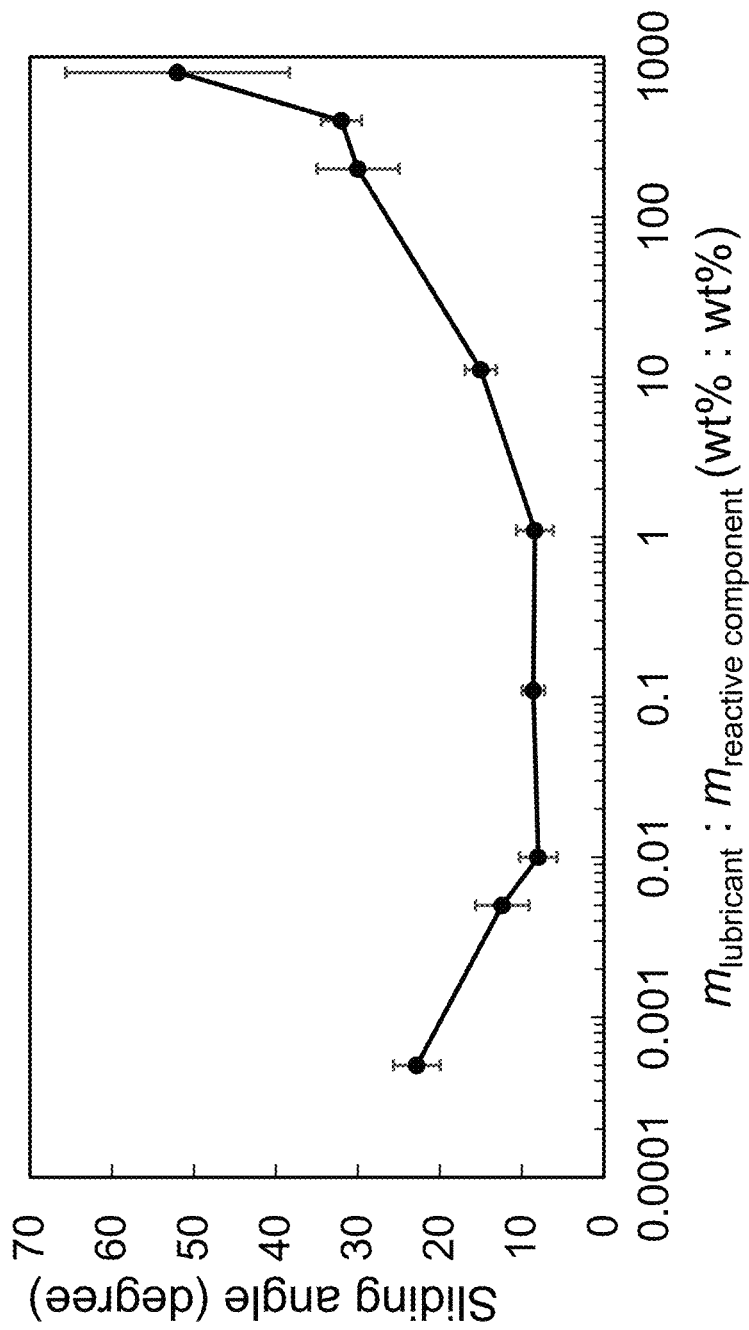
FIG. 4 is a chart showing water sliding angles versus a ratio of lubricant to reactive components in formulations used to prepare repellent coatings. The volume of the water droplets used was 20 μL.

FIG. 4 is a plot showing sliding angles as a function of mass ratio between lubricant and reactive component prepared from all-in-one formulations which include reactive components, catalyst, solvent, and lubricant. For the data in the plot, the reactive monomer, solvent, catalyst, and the lubricant were dimethyldimethoxysilane, isopropanol, sulfuric acid, and silicone oil, respectively. It was observed from data of the formulations that when the mass ratio ($m_{lubricant}/m_{reactive\_component}$) is within the range of about 0.01 to about 1, the sliding angle of a 20 µL water droplet is smaller than 10 degree. Note that the weight ratio of other components are constant, solvent (wt %):reactive component (wt %):catalyst (wt %)=100:10:1. Error bars represent standard deviation of 5 independent measurements.

These examples show that repellent coatings on a surface of a substrate can advantageously be formed with a single formulation with a single application therefrom under ambient conditions (i.e., in air under atmospheric pressures and ambient temperatures) and with liquid-phase processing thereby avoiding complex equipment and processing conditions.

In real world applications, an all-in-one formulation including a fragrance was applied to toilets, sinks, fixtures, and mirrors or glass including windshields, windows in a building, solar panel, brass handrail, and an optical lens for a camera, and medical devices such as ostomy appliances and personal protective equipment such as crocs safety footwear. The coatings were applied onto these surfaces by spray-coating or wiping. The following formulations were coated on the following substrate surfaces.

Example 6: Toilet Coating

| Component | Approximate Concentration |
|---|---|
| Reactive Monomer: dimethyldimethoxysilane | 10 wt % |
| Solvent: isopropanol alcohol | 83 wt % |
| Catalyst: sulfuric acid | 1 wt % |
| Lubricant: silicone oil | 5 wt % |
| Fragrance | 1 wt % |

Example 7: Sink and Fixture Coating

| Component | Approximate Concentration |
|---|---|
| Reactive Monomer: dimethyldimethoxysilane | 10 wt % |
| Solvent: isopropanol alcohol | 86 wt % |
| Catalyst: sulfuric acid | 1 wt % |
| Lubricant: silicone oil | 2 wt % |
| Fragrance | 1 wt % |

Example 8: Mirror/Glass Coating

| Component | Approximate Concentration Range |
|---|---|
| Reactive Monomer: dimethyldimethoxysilane | 10 wt % |
| Solvent: isopropanol alcohol | 87-88 wt % |
| Catalyst: sulfuric acid | 1 wt % |
| Lubricant: silicone oil | 0.05 wt %-0.5 wt % |
| Fragrance | 1 wt % |

Formulations having the components and concentrations of examples 6, 7, 8 were applied to ceramic toilets, ceramic sinks and glass mirrors, respectively. Prior to application of the formulations, the uncoated surfaces were cleaned by wiping with isopropanol or glass cleaner, then allowed to dry. The formulations were applied to the clean dry surface by spraying the formulation followed by wiping, or by directly wiping the formulation on the surfaces with a paper towel, cloth, sponge, or any other similar fabric. Any undesirable residual haze on the surface was removed by wiping or rinsing with isopropanol or glass cleaner followed by wiping with a paper towel, cloth, sponge, or any other similar fabric.

After application of the formulations, the toilets, sinks and mirror were allowed to dry under ambient conditions (e.g., about 23° C., 60% relative humidity, atmospheric pressure) for about 5 min. After drying, repellent coatings were formed on surfaces of the toilets, sinks and mirrors using formulations of examples 6, 7 and 8, respectively. All of the coated surfaces can repel water droplets >15 µL. Further, the lubricant was stable on the surfaces and did not dewet. The resulting coating can repel a broad range of liquids and solids.

Example 9: Polymeric Surfaces

Substrates with relatively unreactive surfaces can also benefit from the formulations and repellent coatings of the present disclosure. For these examples, a reactive coupling layer is applied to the substrate surface prior to applying the formulation. Reactive coupling layers including a silica coupling layer, a poly(ethylene-vinyl acetate) coupling layer and a poly(vinyl alcohol) coupling layer were applied to a polymeric substrate.

For example, a nylon substrate was first treated with a silica coupling layer. The silica layer was formed on a nylon sheet with a sol-gel process. Specifically, a nylon sheet was dip coated or wipe coated with a solution containing TEOS (tetraethyl orthosilicate)/ethanol/$H_2O$/HCl (volume ratio 1:4:6:0.1). Following dip coating, the nylon substrate was cured at room temperature for 12 hours. Multiple silica layers could be applied onto one another by repeating this procedure in order to increase the silica layer thickness.

In another example, a silica coupling layer was formed on the plastic surface of an ostomy pouch (available from Hollister, Inc.) by dip coating the ostomy bag with a solution containing TEOS (tetraethyl orthosilicate)/ethanol/$H_2O$/HCl (volume ratio 1:4:6:0.1).

In another example, a poly(ethylene-vinyl acetate) (PEVA) coupling layer was formed on a nylon sheet by melting and baking PEVA beads (sigma Aldrich, vinyl acetate 40 wt. %) onto the nylon sheet in an oven at 120° C. for 1 hour.

Formulations having the components and concentrations of Example 2 above were then applied to the polymeric substrate surfaces with the various coupling layers by dip coating or spraying or wiping the formulation on to the surfaces. All the coated polymeric surfaces formed repellent surfaces exhibiting a low sliding angle (<25°) against 15 µL water droplets (Table 4).

The aforementioned coating methods are also applicable to polyurethane, polycarbonate, polypropylene, high density polyethylene, polyvinyl chloride, EVA film, poly(methyl methacrylate), silicone (see Table 4).

TABLE 4

Sliding angles on polymeric surfaces having repellent coatings:

| | Reactive coupling layer | |
|---|---|---|
| Polymeric surfaces | Sol gel (silicon dioxide) Sliding angle (degree) | PEVA Sliding angle (degree) |
| Nylon | 20 | 18 |
| Polyurethane | 13 | 17 |
| Polycarbonate | 21 | 18 |
| EVA film (poly (ethylene-vinyl acetate) film from USI, Inc.) | 23 | 18 |
| Polypropylene | 15 | 16 |
| poly(methyl methacrylate) | 25 | 18 |
| polyvinyl chloride | 21 | 17 |
| high density polyethylene | 16 | 20 |
| Silicone | 14 | 15 |

In a simulated toilet environment, our coatings were more effective at preventing mineral scaling on glass than uncoated glass surfaces. Specifically, hard water droplets (200 mg/L sodium chloride) can move roughly an order of magnitude faster on repellent coated surfaces than on uncoated surfaces under the testing conditions of interest and evaporate roughly 1.5× slower on repellent coated surfaces than on uncoated surfaces. Fast-moving, slowly evaporating hard water droplets should be more likely to be removed before leaving mineral residue, making repellent coated surfaces more effective in preventing scaling. After 100 hard-water rinse cycles, repellent coated surfaces exhibited a >95% reduction in hard water buildup in terms of area coverage than untreated glass.

Accelerated UV exposure tests were conducted with a 280-400 nm wavelength with the accumulated dosage of 3600 $MJ/m^2$/year at a nominal 31% relative humidity and 22° C. temperature conditions. Contact angle, sliding angle, and contact angle hysteresis test were conducted on repellent coated-glass samples before and after the UV accelerated tests. The contact angles measurements were >100°, with contact angle hysteresis of <10° and slide angle of <10°, and >90-95% optical transmission in 350 nm-1500 nm. These results suggested that the repellent coated-glass samples maintain similar liquid repellency even after the equivalent of 30 months of sun exposure. The measurements were conducted using Optronic Laboratories Monochromator Model OL750-D, S/N 14516191 (Solar Light Company Inc.).

To quantify the static longevity of repellent coated-glass samples made from a formulation provided in Example 2 (with lubricant viscosity from 20 cSt-350 cSt), the samples were stored in ambient conditions (an average temperature and humidity of 23.5° C. and 40%, respectively) for 8 months and weighed periodically to determine lubricant loss due to evaporation. Sliding angle was measured to quantify the liquid repellency using 15 μL water droplets. The sliding angles of the samples remain <10 degrees over the course of 8 months.

To assess repellent coating durability in abrasive conditions, a 200 g weighted sandpaper was placed on repellent coated-glass samples with the abrasive side of the paper facing the samples. We used aluminum oxide sandpaper with 100 grit. Each abrasion cycle comprised of pulling the sandpaper across the samples for 1 second at a speed of ~0.1 m/s. After every few cycles, the sliding angle of a 15 μL water droplet was measured. The repellent coated sample (with formulation Example 2) withstood >700 aggressive abrasion cycles before the sliding angles for the 15 μL droplets reached over 60 degree.

TABLE 5

Summary of performance metrics of repellent coatings of the present disclosure.

| Characteristics | Quantitative/Qualitative Performance |
| --- | --- |
| Repel multiple substances | Aqueous liquids, viscoelastic solids, bacteria, minerals |
| Reduce hard water scaling | >95% (compared to untreated control after 100 hard water flushing cycles) |
| Longevity | >8 months (under room conditions) |
| Abrasive durability | >1000 abrasion cycles (normal force: 2N, sandpaper: 100 grit) |
| UV stability | >30 months |
| Broad applications | Sanitation, automotive, medical, solar energy, construction |

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

The invention claimed is:

1. A formulation comprising: (i) one or more reactive components that can form a bonded layer on a surface in which the bonded layer comprises an array of compounds each compound having one end bound to a surface and an opposite end extending away from the surface; (ii) an acid catalyst; (iii) a solvent; and (iv) a lubricant,
    wherein the one or more reactive components are selected from the group consisting of an alkoxysilane, di-alkoxy silane, tri-alkoxy silane or combinations thereof, and
    wherein the lubricant has a viscosity of at least about 2 cSt when measured at 25° C.

2. The formulation of claim 1, wherein relative amounts of the one or more reactive components to lubricant by weight in the formulation comprises 1 part reactive components to about 0.005 to about 10 parts lubricant.

3. The formulation of claim 1, wherein the formulation comprises 1 part reactive components to about 0.005-10 parts lubricant to about 0.01-1 parts acid catalyst.

4. The formulation of claim 1, wherein the catalyst does not contain a transition metal.

5. The formulation of claim 1, wherein the acid catalyst comprises sulfuric acid, hydrochloric acid, acetic acid, phosphoric acid, nitric acid, or combinations thereof.

6. The formulation of claim 1, wherein the one or more reactive components are one or more dialkyl di-alkoxy silanes that form an array of linear polysilanes or polysiloxanes or a combination thereof covalently bound directly to the surface through hydroxyl groups on the surface of the substrate, and wherein the linear polysiloxanes are not crosslinked along chains thereof.

7. The formulation of claim 1, wherein the one or more reactive components comprise a tri-alkoxy silane.

8. The formulation of claim 1, wherein the lubricant is a silicone oil or a mineral oil or a plant oil or any combination thereof.

9. The formulation of claim 1, wherein the lubricant has a viscosity of from about 5 cSt to about 800 cSt as measured at 25° C.

10. The formulation of claim 1, wherein the lubricant is a silicone oil or a mineral oil and wherein the lubricant has a viscosity of from about 5 cSt to about 800 cSt when measured at 25° C.

11. The formulation of claim 1, wherein the lubricant is a silicone oil or a mineral oil and wherein the lubricant has a viscosity of from about 15 cSt to about 350 cSt when measured at 25° C.

12. The formulation of claim 1, wherein the one or more reactive components are one or more dialkyl di-alkoxy silanes and wherein the lubricant comprises a silicone oil.

13. The formulation of claim 1, wherein the one or more reactive components are one or more dialkyl di-alkoxy silanes, the lubricant comprises a silicone oil or mineral oil, and wherein the lubricant has a viscosity of from 5 cSt to 800 cSt as measured at 25° C.

14. The formulation of claim 1, wherein the one or more reactive components are one or more dialkyl di-alkoxy silanes, the lubricant comprises a silicone oil, and wherein the lubricant has a viscosity of from 5 cSt to 800 cSt as measured at 25° C.

15. The formulation of claim 1, further comprising a fragrance.

16. The formulation of claim 1, wherein the formulation has shelf-life of over 12 months.

* * * * *